(12) United States Patent
Pieper et al.

(10) Patent No.: US 8,404,916 B1
(45) Date of Patent: Mar. 26, 2013

(54) PROCESS FOR SEPARATING AND/OR INTRODUCING A FLUSH MATERIAL IN AN ADSORPTION SEPARATION SYSTEM

(75) Inventors: Jeffrey L. Pieper, Des Plaines, IL (US); Cynthia K. Zimmerman, Palatine, IL (US); Stephen W. Sohn, Arlington Heights, IL (US); Steven P. Lankton, Wheeling, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/310,954

(22) Filed: Dec. 5, 2011

(51) Int. Cl.
*C07C 7/12* (2006.01)

(52) U.S. Cl. ........ 585/822; 585/820; 585/825; 585/829; 585/830; 585/831

(58) Field of Classification Search .................. None
See application file for complete search history.

(56) References Cited

U.S. PATENT DOCUMENTS

| | | |
|---|---|---|
| 5,171,922 A | 12/1992 | Anderson |
| 5,177,295 A | 1/1993 | Oroskar |
| 5,510,564 A | 4/1996 | Raghuram |
| 6,483,002 B1 * | 11/2002 | O'Brien ........................ 585/826 |
| 7,960,601 B2 | 6/2011 | Noe |

* cited by examiner

*Primary Examiner* — Tam M Nguyen
(74) *Attorney, Agent, or Firm* — Arthur E Gooding

(57) ABSTRACT

Embodiments of the present invention provide, for an adsorption separation system for separating normal paraffins from a hydrocarbon feed stream, a process for switching the adsorption separation from a triple split desorbent system to a dual split desorbent system, and vice versa. Switching occurs by separating and/or introducing a second flush material in the adsorption separation system. This switching can occur during normal operations.

16 Claims, 2 Drawing Sheets

PROCESS FOR SEPARATING AND/OR INTRODUCING A FLUSH MATERIAL IN AN ADSORPTION SEPARATION SYSTEM

FIELD OF THE INVENTION

This invention relates to adsorption separation systems. Specifically, the invention relates to controlling an adsorption separation system by separating a flush material from the system.

BACKGROUND OF THE INVENTION

The production of normal paraffins provides the ability of upgrading products from straight runs of hydrocarbon feed streams derived from crude oil fractionation. For example, straight run kerosene can be further processed to separate out normal paraffins for higher valued products, such as used in the production of linear alkyl benzenes (LAB). Normal paraffins in a particular range (e.g., C10 to C13) are important precursors to LAB production, which is in turn used to produce linear alkyl benzene sulfonate (LAS). LAS is the predominant surfactant used in the production of detergents.

The large utility of detergents and other cleaners has led to extensive development in the areas of detergent production and formulation. While detergents can be formulated from a wide variety of different compounds, much of the world's supply is formulated from chemicals derived from alkylbenzenes. The compounds are produced in petrochemical complexes in which an aromatic hydrocarbon, typically benzene, is alkylated with an olefin of the desired structure and carbon number for the side chain. Typically the olefin is actually a mixture of different olefins forming a homologous series having a range of three to five carbon numbers. The olefin(s) can be derived from several alternative sources. For instance, they can be derived from the oligomerization of propylene or butenes from the polymerization of ethylene. Economics has led to the production of olefins, where the dehydrogenation of the corresponding paraffin is the preferred route to produce the olefin.

Recovery of the desired normal paraffins from a hydrocarbon such as kerosene is performed by adsorption separation, which is one process in overall production of LABs. In a typical adsorption separation process, selected paraffins are separated from branched-chain and cyclic hydrocarbons by adsorption. The paraffins are then passed through a catalytic dehydrogenation zone wherein some of the paraffins are converted to olefins. The resultant mixture of paraffins and olefins is then passed into an alkylation zone in which the olefins are reacted with the aromatic substrate. This overall flow is shown in U.S. Pat. No. 5,276,231, which is incorporated by reference in its entirety, directed to an improvement related to the adsorptive separation of byproduct aromatic hydrocarbons from the dehydrogenation zone effluent, PCT International Publication No. WO 99/07656 indicates that paraffins used in this overall process may be recovered through the use of two adsorptive separation zones in series, with one zone producing normal paraffins and another producing monomethyl paraffins.

In an example adsorption separation process, a hydrocarbon feed stream (e.g., kerosene) is passed through an adsorption separation unit of an adsorption separation system. Nonlimiting examples of adsorption separation units use simulated moving bed technology in a fixed bed system. The adsorption separation unit uses a suitable solid adsorbent (stationary phase) and a desorbent (mobile phase) to separate normal paraffins from a raffinate. More particularly, the adsorption separation unit creates an extract stream including normal paraffins in a desired range and a combined desorbent, as well as a raffinate stream including non-normal paraffins (e.g., branched and cyclic hydrocarbons) and a combined desorbent.

A nonlimiting example combined desorbent in a process for extracting normal paraffins from a hydrocarbon feed stream includes a desorbent material, such as normal pentane, and typically also includes one or more flush materials. These flush materials are selected to move through the adsorption separation system to clear out material from the hydrocarbon feed stream that has not been adsorbed before a desorbent zone passes. The flush materials also keep the desorbent material from breaking through to the adsorption zone, preventing a resulting loss of the normal paraffin product. Non-limiting example flush materials include iso-octane and a mixture of iso-octane and an aromatic, such as paraxylene (p-xylene). One of the flush materials (or the only flush material, if only one is used), e.g., iso-octane, combines with the desorbent material to provide a desorbent mixture, which is used as a desorbent during a desorbent zone of the adsorption separation process.

The extract stream is passed to an extract separation column, for instance a fractionation column. To provide a normal paraffin product, the extract separation column separates the normal paraffin product from the combined desorbent. The raffinate stream is passed to a raffinate separation column, for instance a fractionation column. The raffinate separation column separates the raffinate from the combined desorbent.

Combined desorbents from the extract separation column and the raffinate separation column are processed to separate the desorbent material from the flush materials. If the adsorption separation system employs a combined desorbent that includes a desorbent material (e.g., normal pentane) and a single flush material (e.g., iso-octane), a dual split desorbent system is provided. On the other hand, if the adsorption separation system employs a combined desorbent that includes a desorbent material and two flush materials (e.g., iso-octane and an aromatic, such as paraxylene), a triple split desorbent system is provided.

The triple split desorbent system provides lower aromatics in the normal paraffins product, e.g., <1500 wt ppm aromatics, compared to the dual split desorbent system. However, the triple split desorbent system has the disadvantage of higher utilities, e.g., roughly 10-15% higher fuel and power consumption. For many applications, higher aromatics than that produced by the triple split desorbent system are acceptable, e.g., <5000 wt ppm, and this range is easily achieved by the dual split desorbent system.

Thus, the dual split desorbent system may be preferable where higher aromatics are acceptable, and the triple split desorbent system may be preferable when lower aromatics are required. Currently, however, there is not a way to switch easily from a dual split desorbent system to a triple split desorbent system, or vice versa.

SUMMARY OF THE INVENTION

Embodiments of the invention provide, among other things, processes for switching an adsorption separation system from a dual split system to a triple split system, or vice versa. This is accomplished by separating and/or introducing a second flush material in the adsorption separation system.

An example embodiment of the present invention provides a process for separating a second flush material from a combined desorbent in an adsorption system. The adsorption separation system comprises an adsorption separation unit, an extract separation column, and a raffinate separation column.

To separate the second flush material, at least one of the extract separation column side cut stream comprising the combined desorbent and the raffinate separation column side cut stream comprising the combined desorbent (in other words, the extract separation column side cut stream only, the raffinate separation column side cut stream only, or both the extract separation column and raffinate separation column side cut streams) is passed to a desorbent splitter column. The combined desorbent comprises a desorbent material and first and second flush materials. The desorbent material is separated from the first and second flush materials to provide a desorbent splitter column overhead stream comprising the desorbent material. The second flush material is separated from the first flush material. The separated first flush material is reintroduced into the adsorption system, and the separated second flush material is stored in a second flush material storage tank without being reintroduced into the adsorption separation system. The separated first flush material in particular example embodiments is reintroduced in a desorbent makeup stream. In particular example embodiments the separated first flush material is reintroduced into the raffinate separation column.

In an example process, the adsorption separation unit receives a hydrocarbon feed stream and passes an extract stream to the extract separation column and a raffinate stream to the raffinate separation column. The extract stream comprises normal paraffins and a combined desorbent that comprises a desorbent material and first and second flush materials, and the raffinate stream comprises a raffinate and the combined desorbent. The extract separation column separates the normal paraffins from the extract stream and passes an extract separation column bottoms stream comprising the normal paraffins, an extract separation column overhead stream comprising a desorbent mixture including the desorbent material and the first flush material, and an extract separation column side cut stream comprising the combined desorbent. The raffinate separation column separates the raffinate from the raffinate stream and passes a raffinate separation column bottoms stream comprising the raffinate, a raffinate separation column overhead stream comprising the desorbent mixture, and the raffinate separation side cut stream comprising the combined desorbent.

In example embodiments, the desorbent material comprises normal pentane, the first flush material comprises iso-octanes, and the second flush material comprises an aromatic compound.

Another example embodiment of the invention provides a process for introducing a second flush material to a combined desorbent in an adsorption separation system. At least one of the extract separation column side cut stream comprising the combined desorbent and the raffinate column side cut stream comprising the combined desorbent is passed to a desorbent splitter column. The combined desorbent comprises a desorbent material and first and second flush materials. The desorbent material is separated from the first and second flush materials to provide a desorbent splitter column overhead stream comprising the desorbent material. The second flush material is separated from the first flush material and is stored in a second flush material storage tank. The separated first flush material and the second flush material in the second flush material storage tank are reintroduced into the adsorption separation system. In particular example embodiments, the first flush material and the second flush material are reintroduced in a desorbent makeup stream. In particular example embodiments, the first flush material and the second flush material are reintroduced into the raffinate separation column.

In an example process, the adsorption separation unit receives a hydrocarbon feed stream and passes an extract stream to the extract separation column and a raffinate stream to the raffinate separation column. The extract stream comprises normal paraffins and a combined desorbent that comprises a desorbent material and first and second flush materials, and the raffinate stream comprises a raffinate and the combined desorbent. The extract separation column separates the normal paraffins from the extract stream and passes an extract separation column bottoms stream comprising the normal paraffins, an extract separation column overhead stream comprising a desorbent mixture including the desorbent material and the first flush material, and an extract separation column side cut stream comprising the combined desorbent. The raffinate separation column separates the raffinate from the raffinate stream and passes a raffinate separation column bottoms stream comprising the raffinate, a raffinate separation column overhead stream comprising the desorbent mixture, and a raffinate separation side cut stream comprising the combined desorbent.

In example embodiments, the desorbent material comprises normal pentane, the first flush material comprises iso-octanes, and the second flush material comprises an aromatic compound.

These processes allow an operator to switch the adsorption separation system from a dual split desorbent system to a triple split desorbent system, and vice versa, using standard operations, and with limited modifications to existing adsorption separation systems. Flexibility of operations is provided, allowing both a dual split desorption system and a triple split desorption system, along with the ability to switch between these types during continuous operation of the adsorption separation system. The optimal system for particular aromatics requirements can be selected and employed.

Other embodiments of the invention provide a process for introducing a desorbent makeup stream in an adsorption separation system comprising an adsorption separation unit, an extract separation column, and a raffinate separation column. At least one of an extract separation column side cut stream comprising the combined desorbent and a raffinate separation column side cut stream comprising the combined desorbent is passed to a desorbent splitter column. The combined desorbent comprises a desorbent material, a first flush material, and an amount of a second flush material that is zero or greater. The desorbent material is separated from the first and second flush materials in the desorbent splitter column to provide a desorbent splitter column overhead stream comprising the desorbent material. If the amount of the second flush material in the combined desorbent is greater than zero, the second flush material is separated from the first flush material.

A selected amount of the separated first flush material is passed as a first flush material feed stream, and a selected amount of the separated second flush material is passed as the second flush material feed stream. The selected amount of the second flush material is zero or greater. A selected amount of a desorbent mixture including the desorbent material and the first flush material is passed as a desorbent mixture feed stream. The selected amount of the desorbent mixture feed stream is zero or greater. The selected amounts of the first flush material, the second flush material, and the desorbent mixture provide the desorbent makeup stream. The desorbent makeup stream is introduced into the adsorption separation system.

In an example process, the adsorption separation unit receives a hydrocarbon feed stream and passes an extract stream to the extract separation column and a raffinate stream to the raffinate separation column. The extract stream comprises normal paraffins and a combined desorbent that comprises a desorbent material and first and second flush materials, and the raffinate stream comprises a raffinate and the combined desorbent. The extract separation column separates the normal paraffins from the extract stream and passes an extract separation column bottoms stream comprising the normal paraffins, an extract separation column overhead stream comprising a desorbent mixture including the desorbent material and the first flush material, and an extract separation column side cut stream comprising the combined desorbent. The raffinate separation column separates the raffinate from the raffinate stream and passes a raffinate separation column bottoms stream comprising the raffinate, a raffinate separation column overhead stream comprising the desorbent mixture, and a raffinate separation side cut stream comprising the combined desorbent. A portion of the raffinate separation column is passed to a desorbent mixture storage tank. Passing the selected amount of the desorbent mixture in this example process comprises passing the selected amount of the desorbent mixture from the desorbent mixture storage tank.

In example embodiments, the desorbent material comprises normal pentane, the first flush material comprises iso-octanes, and the second flush material comprises an aromatic compound.

If the selected amount of the second flush material is zero, for instance, the adsorption separation system can be switched to a dual split desorption system. If the selected amount of the second flush material is greater than zero, the adsorption system can be switched to a triple split desorption system. The amount of the first flush material in a dual split desorption system can also be altered using this example process.

Additional objects, embodiments, and details of this invention can be obtained from the following drawing and detailed description of the invention.

DETAILED DESCRIPTION OF THE INVENTION

Embodiments of the present invention provide, for an adsorption separation system, a process for switching the adsorption separation from a triple split desorbent system to a dual split desorbent system, and vice versa. The adsorption separation system can be, for example, a system for separating normal paraffins from a hydrocarbon feed stream. By providing processes to switch between a dual split desorbent system and a triple split desorbent system, a particular system can be selected that is either tailored to lower operating costs, e.g., 10 to 15% lower fuel and power utilities for a dual split desorbent system, or to lower aromatics in the normal paraffin product for a triple split desorbent system. This switching can occur during normal operations and can be completed within, for instance, 2 to 4 days. Embodiments of the invention also include a process for providing a desorbent makeup stream to an adsorption separation system.

Generally, the switching between dual and triple split desorption systems is provided by separating a second flush material from a first flush material in a combined desorbent. The switching generally occurs by the second flush material being either omitted from or reintroduced into the adsorption separation system. A nonlimiting example combined desorbent includes a desorbent material, such as normal pentane, that is combined (e.g., mixed) with flush materials. As used herein, "flush materials" is intended to refer to either a first flush material or a mixture of first and second flush materials. Nonlimiting examples for the first flush material are iso-octanes, and nonlimiting examples for the second flush material are aromatic compounds, e.g., paraxylene (p-xylene), though "first" and "second" should not be construed as necessarily requiring a particular order for the flush materials.

Figure 1:
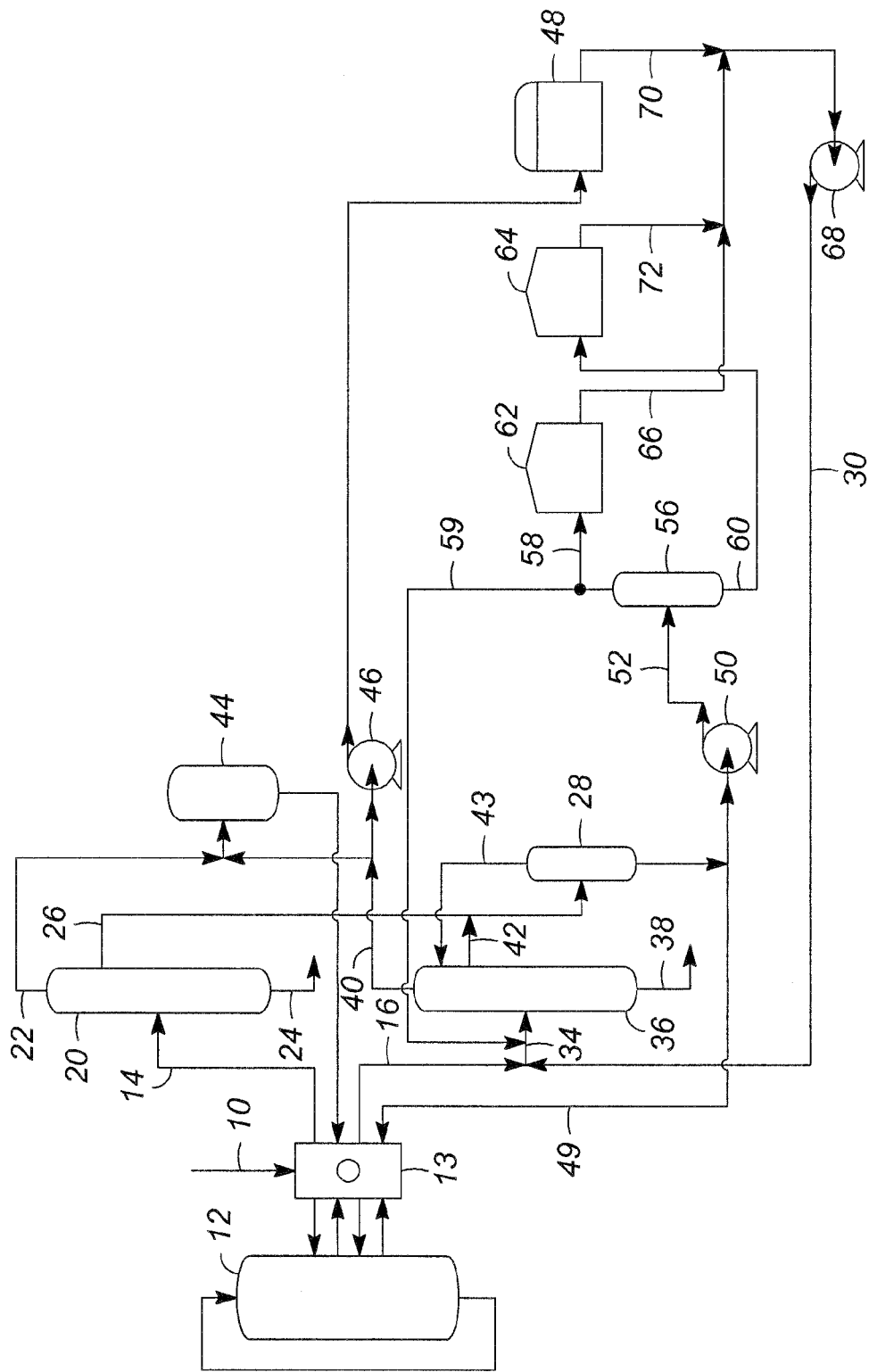
FIG. 1 is a diagram of a first embodiment of the invention as an example process for separating normal paraffins from a hydrocarbon feed stream in an adsorption separation system.

FIG. 1 shows an example process in an adsorption separation system for producing a normal paraffin (n-paraffin) product from a hydrocarbon feed stream 10, including processes for switching between a dual split desorption system and a triple split desorption system and vice versa. The hydrocarbon feed stream 10, which is selected for its content of normal paraffins, is passed to an adsorption separation unit 12. A rotary valve system 13, part of the adsorption separation unit 12, controls the positions of the inflows to and outflows from the adsorption separation unit.

The adsorption separation unit 12 includes a solid adsorbent (stationary phase), and liquid adsorption, purification, desorption, and buffer (mobile phase) zones. A nonlimiting example adsorption separation unit 12 uses a simulated moving bed technique with an adsorbent selected for separating the desired normal paraffins from the hydrocarbon feed stream 10.

The purification zone in the example adsorption separation process is embodied in a flush zone, which moves through the adsorption separation system like the adsorption and desorption zones, and is between these zones. The flush zone clears out the material from the hydrocarbon feed stream 10 that has not been adsorbed by the adsorption separation unit 12 before the desorption zone passes. The flush zone also keeps the desorbent from breaking through to the adsorption zone, whereas if the desorbent were to break through to the adsorption zone, the example process would experience a loss of the normal paraffin product. An example flush zone has a hydrocarbon that will not displace the adsorbed material while it is displacing the non-adsorbed portion of the hydrocarbon feed stream 10. This flush zone hydrocarbon preferably is an intermediate non-normal hydrocarbon, such as iso-octane, or an aromatic compound in the C7 to C8 range, but it can also include non-normal hydrocarbons outside the C7 to C8 range and can include napthenes and aromatics. Examples of flush materials include the first flush material or a mixture of the first and second flush materials, i.e., iso-octanes or mixtures of iso-octanes and aromatics.

The desorption zone employs a desorbent mixture, which includes a mixture of the desorbent material (e.g., normal pentane) and the first flush material (e.g., iso-octane). Nonlimiting example ratios of this desorbent mixture range from 50/50 to 70/30 (vol/vol) desorbent material to first flush material. As used herein, "desorbent mixture" is intended to refer to a mixture of the desorbent material and the first flush material used that is used as a desorbent during the desorption zone, even though the particular proportions of the desorbent material and the first flush material may vary at different points during the overall adsorption separation process. Further, the purification zone employs a first flush material (e.g., iso-octane) in a dual split desorbent system or a mixture of the first flush material (e.g., iso-octane) and second flush material (e.g., paraxylene) in a triple split desorbent system. Nonlimiting example ratios of the combined flush mixture range from 90/10 to 30/70 (vol/vol) first flush material to second flush material. The flush materials combine (e.g., mix) with the desorbent material to provide a combined desorbent. "Combined desorbent" as used herein refers generally to a mixture of the desorbent material and the flush materials (that is, amounts of both the first flush material and the second flush material, if the second flush material is present) that appears in the adsorption separation process, even though the particular proportions of the desorbent material, the first flush material, and the second flush material may vary at different points during the adsorption separation process.

The adsorption separation unit 12 creates an extract stream 14 that includes n-paraffins in the selected range and the combined desorbent. The adsorption separation unit 12 also creates a raffinate stream 16 that includes non-normal paraffins and the combined desorbent. The extract stream 14 is passed to an extract separation column 20, which is operated at desorbent separation conditions to create an extract separation column overhead stream 22 (or net desorbent stream) that includes the desorbent mixture, e.g., a mixture of normal pentane and iso-octane. The extract separation column 20 also creates an extract separation column bottoms stream 24 that includes the n-paraffins in the selected carbon range (n-paraffin product).

Further, the extract separation column 20 creates an extract separation column side cut stream 26 that includes the combined desorbent. This extract separation column side cut stream 26 is passed to a desorbent splitter column 28. The desorbent splitter column 28 operates under suitable desorbent splitting conditions to separate the desorbent material from the flush materials (i.e., the first flush material, or a mixture of the first and second flush materials) in the combined desorbent.

To introduce, or reintroduce, desorbent into the multi-desorbent system, the raffinate stream 16 is combined with a desorbent makeup stream 30 to provide an intermediate raffinate stream 34. This intermediate raffinate stream 34 is passed to a raffinate separation column 36. The raffinate separation column 36 is operated at desorbent separation conditions to create a raffinate separation column bottoms stream 38 including the raffinate, a raffinate separation column overhead stream 40 (or net desorbent stream) including the desorbent mixture, and a raffinate separation column side cut stream 42 that includes the combined desorbent. The desorbent mixture in the raffinate separation column overhead stream 40 may have different proportions of the desorbent material and the first flush material as the desorbent mixture in the extract column overhead stream 22. The raffinate column side cut desorbent stream 42 is passed with the extract separation column side cut stream 26 to the desorbent splitter column 28.

The example desorbent splitter column 28 is a column having around 20 trays (e.g., sieve trays). The column bottoms is heated by a thermosiphon type reboiler, in some embodiments using the raffinate stream 38 as the heating medium but could also be another hotter process stream or heating medium (e.g. hot oil) to boil, or vaporize, the liquid at the bottom of the column to provide an upflowing vapor stream. An example bottoms composition is 30 to 90 wt % iso-octane and 10 to 70 wt % paraxylene for a triple split desorbent system and at least 95 wt % iso-octane for a dual split desorbent system. Bottoms temperature of the desorbent splitter column 28 is between 135 to 185° C. (275 to 360° F.). The operating pressure at the top of the desorbent splitter column 28 is between 1.4 barg to 1.7 barg (20 to 25 psig) with the overhead vapor line connecting to the middle section of the raffinate separation column. The extract separation column side cut stream 26 and the raffinate column side cut stream 42 are combined and fed to the top tray. The desorbent splitter column 28 separates the desorbent material, providing a desorbent splitter column overhead stream 43, including the desorbent material (e.g., normal pentane), which is passed to the raffinate column 36.

A portion of the raffinate separation column overhead stream 40 is passed with the extract separation column overhead stream 22 to a desorbent surge drum 44 that stores the desorbent mixture. The desorbent surge drum 44 provides a surge capacity to supply the desorbent mixture (e.g., via a desorbent mixture pump (not shown)) to the adsorption separation unit 12. Another portion of the raffinate separation column overhead stream 40 passes to a raffinate column net overhead pump 46, which pumps the raffinate separation column overhead stream to a desorbent mixture storage tank 48 that stores the desorbent mixture. In other example embodiments, the raffinate separation column overhead pumps (not shown) are used to provide both reflux to the raffinate separation column 36 and pump the raffinate separation column overhead stream 40 to a desorbent mixture storage tank 48. The desorbent mixture storage tank 48 and the raffinate column net overhead pump 46 pass (e.g., drags) desorbent from the overhead of the raffinate separation column 36 to maintain desorbent mixture levels at reasonable working levels.

In addition to the desorbent splitter column overhead stream 43, the desorbent splitter column 28 creates a first desorbent splitter column bottoms stream 49 including the flush materials, which is passed to the adsorption separation unit 12 for the flush zone. Further, a flush pumpout pump 50, for instance a low head pump, at the bottom of the desorbent splitter column 28 drags a portion of the flush materials as a second desorbent splitter column bottoms stream 52 and passes it to a flush splitter column 56 for separating feed streams of the first and second flush materials. An example flush pumpout pump 50 is a low discharge head pump (e.g., a centrifugal type pump) having a discharge pressure within the design pressure and temperature rating of the piping to the flush splitter 56 and to storage tanks. A pump (not shown) that delivers the first desorbent splitter column bottoms stream 49 to the adsorption separation unit 12, by contrast, in an example embodiment is a multi-stage high head pump.

The flush splitter column 56 is operated at suitable conditions for separating the first and second flush materials feed streams, e.g., iso-octane and paraxylene feed streams, from the (mixture of) flush materials.

The example flush splitter column 56 creates a flush splitter overhead stream 59 that includes the first flush material, such as an iso-octane rich stream, and a flush splitter bottoms stream 60 that includes the second flush material, such as a paraxylene rich stream. As an example, the flush splitter column 56 is a fractionation column having around 20 trays (e.g. sieve trays). The column is heated by a thermosiphon type reboiler using a heating medium (e.g. hot oil) or another hotter process stream for energy efficiency to boil, or vaporize, the liquid at the bottom of the column to provide an upflowing vapor stream. The bottoms composition contains at least 90 wt % paraxylene. The bottoms temperature is between 155 to 185° C. (310 to 365° F.). An overhead condensing system using an air cooled condenser is used to condense the vapor in the column overhead to provide reflux to the column. The operating pressure at the top of the column is between 1.4 barg to 1.7 barg (20 to 25 psig). The overhead composition will contain at least 95 wt % iso-octane.

The flush splitter overhead stream 59 is recycled back to the raffinate separation column 38 to reintroduce the separated first flush material into the adsorption separation system. A portion or all of the flush splitter overhead stream 59 can also be diverted in another flush splitter overhead stream 58 and is passed to a first flush material storage tank 62, for instance an iso-octane storage tank, for storing the first flush material. The flush splitter bottoms stream 60 is passed to a second flush material storage tank 64, for instance a paraxylene storage tank, for storing the second flush material. The first and second flush material storage tanks 62, 64 in a nonlimiting example can be atmospheric closed-roof type storage tanks. An example tankage section in the adsorption separation system includes the first and second flush material storage tanks 62, 64, the desorbent mixture storage tank 48 storing the desorbent mixture, and a separate purified desorbent tank (not shown) for storing the desorbent material (e.g., normal pentane).

Concurrently with the operation of the adsorption separation unit 12, the extract separation column 20, the raffinate separation column 36, the desorbent splitter column 28, and the flush splitter column 56, the desorbent makeup stream 30 is passed to the raffinate separation column 36. To provide the desorbent makeup stream 30, a first flush material feed stream 66 is passed from the first flush material storage tank 62 to a desorbent makeup pump 68.

Further, the second flush material can be selectively added to the adsorption separation system by passing a second flush material feed stream 72 from the second flush material storage tank 64 to provide the desorbent makeup stream 30. The desorbent mixture material can also be selectively added to the adsorption separation system by passing the desorbent mixture feed stream 70 from the desorbent mixture storage tank 48 to provide the desorbent makeup stream 30.

Additionally, a purified desorbent feed stream (not shown) from a purified desorbent storage tank (not shown) can be used for the desorbent makeup stream 30. In an example embodiment, a laboratory analysis of material in the desorbent surge drum 44 can be used to determine if a desired desorbent mixture is present.

The selected amounts of the first flush material feed stream 66, the second flush material feed stream 72, the desorbent mixture feed stream 70, and/or the purified desorbent feed stream (not shown) are pumped individually by the desorbent makeup pump 68, and passed as the desorbent makeup stream 30 to the raffinate separation column 36. This introduces the desorbent makeup stream 30 to the adsorption separation system. As selected amounts, and not necessarily all, of the separated first flush material, the separated second flush material, the separated desorbent mixture, and/or purified desorbent can be reintroduced, it should be understood that, as used herein, reintroducing the separated material or mixture need not require reintroducing all of the material or mixture that has been previously separated into the adsorption separation system.

Thus, the adsorption separation system can be switched from a triple split desorbent system to a dual split desorbent system by separating the second flush material from the combined desorbent and reintroducing the first flush material into the adsorption separation system. This can be performed by separating the desorbent material from the flush materials in the combined desorbent using the desorbent splitter 28, passing (e.g., dragging via the flush pumpout pump 50) the flush materials from the bottom of the desorbent splitter to provide the second desorbent splitter bottom stream 52 to the flush splitter 56, separating the second flush material from the first flush material using the flush splitter, recycling the first flush material to the raffinate separation column 36 or storing a portion of the first flush material in the first flush material storage tank 62, storing the separated second flush material in the second flush material storage tank 64, and reintroducing the first flush material feed stream 66 into the adsorption separation system (e.g., via the flush splitter column overhead stream 59 and/or into the raffinate separation column 36 via the desorbent makeup stream 30), without reintroducing the second flush material. The first flush material can be reintroduced alone or the other desorbent mixture materials added separately to the raffinate separation column 36 to provide the desired desorbent mixture combination. This switching can be part of a continuous process of the adsorption separation system, and can take place as part of standard operations.

The adsorption separation system can be switched from a dual split desorbent system to a triple split desorbent system by introducing stored second flush material into the adsorption separation system for providing a combined desorbent. This can be performed by passing the second flush material feed stream 72 from the second flush material storage tank 64 to provide the desorbent makeup stream 30.

During adding the second flush material, the combined desorbent mixture (e.g., normal pentane and iso-octane) levels can be maintained at reasonable working levels by dragging desorbent from the overhead of the raffinate separation column 36 to the desorbent storage tank 48 using the raffinate column net overhead pump 46.

As with the switch from the triple split desorbent system to the dual split desorbent system, the first flush material, desorbent mixture material, or purified desorbent material can be added in the same manner by the desorbent makeup stream 30 to the adsorption separation unit 12 to provide the desired desorbent mixture combination.

As with the switch to a dual split desorbent system, the switch to a triple split desorbent system can be part of a continuous process of the adsorption separation system, and can take place as part of standard operations.

Further, for a dual-split desorbent system (e.g., where the combined desorbent does not include the second flush material), the flush pumpout pump 50 can be used to adjust the amount of the first flush material by withdrawing the flush material from the desorbent splitter 28. This can be accomplished, for example, by adjusting the amount of the second desorbent splitter column bottoms stream 52 that is pumped by the flush pumpout pump 50 relative to the amount of the first desorbent splitter column bottoms stream 49.

Figure 2:
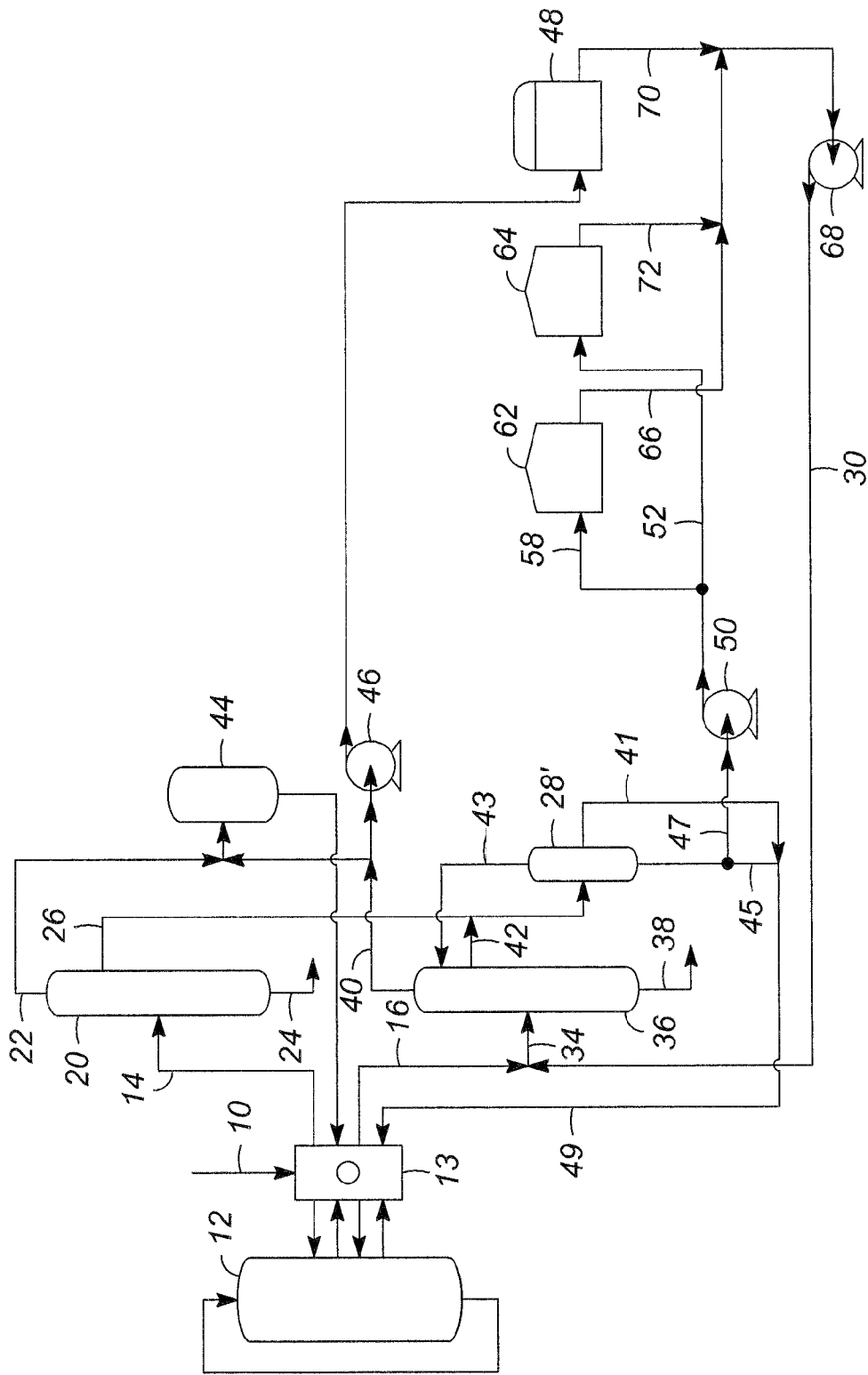
FIG. 2 is a diagram of a second embodiment of the invention.

In a second embodiment as shown in FIG. 2, where analogous parts are illustrated with like reference characters, the design of a desorbent splitter column 28' is modified to add a desorbent splitter side cut stream 41 to eliminate the need for the flush splitter column 56 in FIG. 1.

The extract separation column side cut stream 26 that includes the combined desorbent and the raffinate separation column side cut stream 42 that includes the combined desorbent are fed to desorbent splitter column 28'. The main flow of flush material is taken from the desorbent splitter column side cut stream 41. In normal operating mode for a triple split desorbent system, a second flush material rich desorbent splitter bottoms stream 45 is combined with the desorbent splitter column side cut stream 41 to provide the flush material stream 49.

The example desorbent splitter column 28' is a column having around 30 trays (e.g. sieve trays) with the desorbent splitter side cut stream 41 added. The column bottoms is heated by a thermosiphon reboiler to boil, or vaporize, the liquid at the bottom of the column to provide an upflowing vapor stream. Due to higher bottoms temperature, e.g., between 175 to 185° C. (350 to 365° F.), when operated for the triple split desorbent system, the heating medium chosen is hot oil compared to the raffinate stream 38 used in the embodiment of FIG. 1 to provide enough temperature difference for heating the desorbent splitter column 28'. The operating pressure at the top of the desorbent splitter column 28' is between 1.4 barg to 1.7 barg (20 to 25 psig) with the overhead vapor line connecting to the middle section of the raffinate separation column 36.

In some example embodiments, the raffinate separation column bottoms stream 38, being no longer used for heating the desorbent splitter column 28', is used as the heating medium in a new heat exchanger (not shown) placed in series with a desorbent heater (not shown) to heat the desorbent from the desorbent surge drum 44 to the adsorption separation section 12. This allows a smaller desorbent heater.

When operated with the triple split desorbent system, the desorption splitter column bottoms composition is at least 90 wt % paraxylene. The desorbent splitter column side cut stream 41 composition is 30 to 90 wt % iso-octane and 10 to 70 wt % paraxylene.

When operated with the dual split desorbent system, the desorbent splitter column side cut stream 41 is stopped, and the desorbent splitter bottoms stream 45 provides the flush material stream 49. The desorbent splitter column bottoms stream composition is 30 to 90 wt % iso-octane and 10 to 70 wt % paraxylene.

To switch from a triple split desorbent system to a dual split desorbent system, a net bottoms drag stream 47 rich in the second flush material (e.g. paraxylene) is passed to the flush pumpout pump 50 for removing the second flush material while the desorbent splitter column bottoms stream 45 is reduced or stopped. The flush pumpout pump 50 passes the net bottoms drag stream 47 through stream 52 to the second flush material storage tank 64. As the amount of the second flush material is depleted, as indicated by a lowering of the desorbent splitter column 28' bottoms temperature due to changing composition and also sampling and laboratory analysis to determine the composition, the desorbent splitter column side cut stream 41 is gradually stopped while the amount of desorbent splitter column bottoms stream 45 is increased to maintain the same flush material stream 49 flow as previous. The destination of the net bottoms drag stream 47 can be diverted to the first flush material storage tank 62 by switching the discharge of the flush pumpout pump 50 from stream 52 to stream 58. As determined by sampling, the net bottoms drag stream 47 can be stopped when the amount of the second flush material is reduced to low levels or zero. During the switch, the first flush material (e.g., iso-octane) can be made up to the raffinate separation column 36 from the first flush material storage tank 62.

To switch from a dual split desorbent system to a triple desorbent system, the second flush material (e.g. paraxylene) is made up to the raffinate separation column 36 from the second flush material desorbent storage tank 64. As the amount of the second flush material builds up in the desorbent splitter bottoms, as indicated by an increase in bottoms temperature, and also sampling and laboratory analysis to determine the composition the desorbent splitter column side cut stream 41 is restarted. Any excess first flush material is dragged from the system with the desorbent material by using the raffinate separation column overhead pump 46 and passing the desorbent material to the desorbent storage tank 48.

For both example embodiments of the invention, the operations of both the extract separation column 20 and raffinate separation column 36 should be monitored and adjusted as needed when switching from a triple split desorbent system to a double split desorbent system and vice versa.

As an example, the extract separation column 20 can be a fractionation column having around 60 trays (e.g. sieve trays). The column can be heated by a thermosiphon type reboiler using a heating medium (e.g. hot oil). As another example, the extract separation column 20 can be heated by a fired heater reboiler. The bottoms temperature is 240 to 270° C. (465 to 520° C.). A totally condensing overhead system (not shown) using an air cooled condenser is used to condense the vapor in the column overhead to provide reflux to the column and extract separation column overhead stream 22 (net desorbent stream). The operating pressure at the top of the column is between 1.4 barg to 1.7 barg (20 to 25 psig). The overhead composition will be richer in the desorbent material (e.g. normal pentane).

As a further example, the raffinate separation column 36 can be a fractionation column having around 60 trays (e.g. sieve trays). The raffinate separation column 36 can be heated by a thermosiphon type reboiler using a heating medium (e.g. hot oil). As another example, the raffinate separation column 36 can be heated by a fired heater reboiler. The bottoms temperature is 240 to 270° C. (465 to 520° C.). A totally condensing overhead system using an air cooled condenser is used to condense the vapor in the column overhead to provide reflux to the column and raffinate separation column overhead stream 40 (net desorbent stream). The operating pressure at the top of the raffinate separation column 36 is between 1.4 barg to 1.7 barg (20 to 25 psig). The overhead composition will be roughly equal in the amount of desorbent material (e.g. normal pentane) and first flush material (e.g. iso-octane).

To facilitate faster removal of the second flush material from the adsorption separation unit 12 for the embodiments in both FIG. 1 and FIG. 2, a new head flush out line (not shown) can be added to the top and bottom heads of both chambers in the adsorption separation unit 12.

In some example embodiments, each of the first flush material feed stream 66, the second flush material feed stream 72, the desorbent mixture feed stream 70, and the purified desorbent feed stream (not shown) can be selectively introduced into the desorbent makeup stream 30 or elsewhere in the adsorption separation system, in any of various proportions. To provide desorbent makeup to the adsorbent separation system, a selected amount of previously separated (e.g., by the flush splitter column 56) and stored first flush material from the first flush material storage tank 62 can be passed in a selected amount as the first flush material feed stream 66. A selected amount (which can be zero) of previously separated (e.g., by the flush splitter column 56) and stored flush material from the second flush material storage tank 64 can be passed as the second flush material feed stream 72. If the combined desorbent does not include the second flush material (e.g., if a dual-split system is employed), the second flush material would not be separated. A selected amount (which can be zero) of desorbent mixture, previously separated from the raffinate separation column 36, can be passed as the desorbent mixture feed stream 70. Further, a selected amount of the desorbent material can be introduced via the purified desorbent feed stream (not shown). The desorbent makeup pump 68 passes these selected amounts separately from each of the feed streams 66, 72, 70 and separately from the purified desorbent feed stream to provide the desorbent makeup stream 30 and introduces the desorbent makeup stream into the adsorption separation system, for instance into the raffinate separation column 36.

Control of these proportions combined with selective operation of the flush pumpout pump 50 (to drag the flush materials from the desorbent splitter column 28) and selective operation of the raffinate column overhead pump 46 (to drag desorbent material from the raffinate separation column 36 to the desorbent mixture storage tank 48) allows customization of the combined desorbent mixture as well as the ability to switch between dual split and triple split desorbent systems. Further, even for a dual split desorbent system without switching, the amount of the first flush material can be altered within the system by separating the first flush material and reintroducing a lesser amount to the adsorption separation system.

By providing processes to switch from a dual split desorbent system to a triple split desorption system or vice versa according to embodiments of the invention, a particular system can be selected that is either tailored to lower aromatics, or that is more efficient. Because the example processes can be implemented as part of the continuous operation of the adsorption separation system, they can be smoothly integrated into an overall operation to balance these competing goals, without requiring changes in equipment. Appropriate balance of desorbent material and flush materials can be adjusted as needed and corrected as part of standard operations.

In addition to the continuous adsorption separation system disclosed in particular example embodiments, other adsorption separation processes are also applicable for use in the present invention, and it is intended that the invention covers other adsorption separation systems.

While the invention has been described with what are presently considered the preferred embodiments, it is to be understood that the invention is not limited to the disclosed embodiments, but is intended to cover various modifications and equivalent arrangements included within the scope of the appended claims.

The invention claimed is:

1. A process for separating a second flush material from a combined desorbent in adsorption separation system comprising an adsorption separation unit, an extract separation column, and a raffinate separation column, the process comprising:
    passing at least one of an extract separation column side cut stream comprising the combined desorbent and a raffinate separation column side cut stream comprising the combined desorbent to a desorbent splitter column, the combined desorbent comprising a desorbent material and first and second flush materials;
    separating the desorbent material from the first and second flush materials in the desorbent splitter column to provide a desorbent splitter column overhead stream comprising the desorbent material;
    separating the second flush material from the first flush material;
    storing the separated second flush material in a second flush material storage tank; and
    introducing the separated first flush material into the adsorption separation system without reintroducing the separated second flush material.

2. The process of claim 1, wherein the adsorption separation unit receives a hydrocarbon feed stream and passes an extract stream to the extract separation column and a raffinate stream to the raffinate separation column, the extract stream comprising normal paraffins and the combined desorbent, the raffinate stream comprising a raffinate and the combined desorbent;
    wherein the extract separation column separates the normal paraffins from the extract stream and passes an extract separation column bottoms stream comprising the normal paraffins, an extract separation column overhead stream comprising a desorbent mixture including the desorbent material and the first flush material, and the extract separation column side cut stream comprising the combined desorbent;
    wherein the raffinate separation column separates the raffinate from the raffinate stream and passes a raffinate separation column bottoms stream comprising the raffinate, a raffinate separation column overhead stream comprising the desorbent mixture, and the raffinate separation column side cut stream comprising the combined desorbent.

3. The process of claim 2, further comprising:
    passing a selected amount of the raffinate separation column overhead stream to adjust the ratio of the desorbent and first flush material in the combined desorbent mixture and store the desorbent mixture;
    passing a selected amount of the desorbent mixture in the desorbent mixture storage tank as a desorbent mixture feed stream; and
    passing the desorbent mixture feed stream and at least a portion of the separated first flush material feed stream to provide a desorbent makeup stream;
    wherein said reintroducing the desorbent makeup stream comprises passing the desorbent makeup stream to the raffinate separation column.

4. The process of claim 1, further comprising:
    passing a desorbent splitter column bottoms stream comprising the first and second flush materials to a flush splitter column;
    wherein said separating the second flush material from the first flush material comprises the flush splitter column passing a flush splitter column bottoms stream comprising the separated second flush material and a flush splitter column overhead stream comprising the separated first flush material.

5. The process of claim 1, further comprising:
    the desorbent splitter column passing the desorbent splitter column overhead stream comprising the desorbent material, a desorbent splitter column side cut stream comprising the first and second flush materials, and a desorbent splitter column bottoms stream comprising the second flush material;
    passing the desorbent splitter column side cut stream into the adsorption separation system;
    wherein said storing the separated second flush material comprises storing the second flush material from the desorbent splitter column bottoms stream.

6. The process of claim 1, wherein the desorbent material comprises normal pentane, the first flush material comprises iso-octanes, and the second flush material comprises an aromatic compound.

7. The process of claim 1, wherein the second flush material comprises paraxylene.

8. The process of claim 1, wherein said introducing the separated first flush material is part of a continuous process of the adsorption separation system.

9. A process for introducing a second flush material to a combined desorbent in an adsorption separation system comprising an adsorption separation unit, an extract separation column, and a raffinate separation column, the process comprising:
    passing at least one of an extract separation column side cut stream comprising the combined desorbent and a raffinate separation column side cut stream comprising the combined desorbent to a desorbent splitter column, the combined desorbent comprising a desorbent material and first and second flush materials;

separating the desorbent material from the first and second flush materials in the desorbent splitter column to provide a desorbent splitter column overhead stream comprising the desorbent material;

separating the second flush material from the first flush material;

storing the separated second flush material in a second flush material storage tank; and introducing the separated first flush material and the stored second flush material into the adsorption separation system.

10. The process of claim 9, wherein the adsorption separation unit receives a hydrocarbon feed stream and passes an extract stream to the extract separation column and a raffinate stream to the raffinate separation column, the extract stream comprising normal paraffins and the combined desorbent, the raffinate stream comprising a raffinate and the combined desorbent;

wherein the extract separation column separates the normal paraffins from the extract stream and passes an extract separation column bottoms stream comprising the normal paraffins, an extract separation column overhead stream comprising a desorbent mixture including the desorbent material and the first flush material, and the extract separation column side cut stream comprising the combined desorbent;

wherein the raffinate separation column separates the raffinate from the raffinate stream and passes a raffinate separation column bottoms stream comprising the raffinate, a raffinate separation column overhead stream comprising the desorbent mixture, and the raffinate separation column side cut stream comprising the combined desorbent.

11. The process of claim 10, further comprising:

passing a selected amount of the raffinate separation column overhead stream to a desorbent mixture storage tank to adjust the ratio of the desorbent and first flush material in the combined desorbent mixture and store the desorbent mixture;

passing a selected amount of the stored desorbent mixture as a desorbent mixture feed stream; and passing the desorbent mixture feed stream, the separated first flush material feed stream, and the stored second flush material feed stream to provide a desorbent makeup stream;

passing the desorbent makeup stream to the raffinate separation column.

12. The process of claim 9, further comprising:

passing a desorbent splitter column bottoms stream comprising the first and second flush materials to a flush splitter column;

wherein said separating the second flush material from the first flush material comprises the flush splitter column passing a flush splitter column bottoms stream comprising the separated second flush material and a flush splitter column overhead stream comprising the separated first flush material.

13. The process of claim 9, further comprising:

the desorbent splitter column passing the desorbent splitter column overhead stream comprising the desorbent material, a desorbent splitter column side cut stream comprising the first and second flush materials, and a desorbent splitter column bottoms stream comprising the second flush material;

passing the desorbent splitter column side cut stream into the adsorption separation system;

wherein said storing the separated second flush material comprises storing the second flush material from the desorbent splitter column bottoms stream.

14. The process of claim 9, wherein the desorbent material comprises normal pentane, the first flush material comprises iso-octanes, and the second flush material comprises an aromatic compound.

15. The process of claim 9, wherein the second flush material comprises paraxylene.

16. The process of claim 9, wherein said introducing the separated first flush material and the stored second flush material are part of a continuous process of the adsorption separation system.

* * * * *